US009757610B2

(12) United States Patent
Artemiadis et al.

(10) Patent No.: US 9,757,610 B2
(45) Date of Patent: Sep. 12, 2017

(54) VARIABLE STIFFNESS TREADMILL SYSTEM

(71) Applicant: ARIZONA BOARD OF REGENTS ON BEHALF OF ARIZONA STATE UNIVERSITY, Tempe, AZ (US)

(72) Inventors: Panagiotis Artemiadis, Phoenix, AZ (US); Andrew Barkan, Phoenix, AZ (US)

(73) Assignee: Arizona Board of Regents on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 15/032,934

(22) PCT Filed: Oct. 28, 2014

(86) PCT No.: PCT/US2014/062534
§ 371 (c)(1),
(2) Date: Apr. 28, 2016

(87) PCT Pub. No.: WO2015/065948
PCT Pub. Date: May 7, 2015

(65) Prior Publication Data
US 2016/0243397 A1 Aug. 25, 2016

Related U.S. Application Data

(60) Provisional application No. 61/896,509, filed on Oct. 28, 2013.

(51) Int. Cl.
*A63B 22/02* (2006.01)
*A63B 69/00* (2006.01)
(Continued)

(52) U.S. Cl.
CPC .... *A63B 22/0292* (2015.10); *A63B 21/00181* (2013.01); *A63B 22/02* (2013.01);
(Continued)

(58) Field of Classification Search
CPC . A63B 22/02–22/0292; A63B 69/0064; A63B 24/0087; A63B 21/00181;
(Continued)

(56) References Cited

U.S. PATENT DOCUMENTS 3,408,067 A * 10/1968 Armstrong ............. A63B 22/02
434/253
4,204,673 A * 5/1980 Speer, Sr. .......... A63B 22/0012
198/817
(Continued)

FOREIGN PATENT DOCUMENTS

WO 2008099429 A 8/2008

OTHER PUBLICATIONS

R. Klint et al, "Load Rather Than Length Sensitive Feedback Contributes to Soleus Muscle Activity During Human Treadmill Walking" Journal of Neurophysiology, vol. 103, No. 5, pp. 2747-2756, 2010.
(Continued)

*Primary Examiner* — Stephen R Crow
*Assistant Examiner* — Garrett Atkinson
(74) *Attorney, Agent, or Firm* — Ari M. Bai; Polsinelli PC (57) ABSTRACT

A variable stiffness treadmill system having a variable stiffness mechanism, a split-belt treadmill, a counterweight system, and a body weight support for supporting an individual and varying the stiffness below the individual on the treadmill for research and rehabilitation.

20 Claims, 7 Drawing Sheets

(51) Int. Cl.
  A63B 24/00      (2006.01)
  A63B 21/00      (2006.01)
  A61B 5/00       (2006.01)
  A61B 5/103      (2006.01)

(52) U.S. Cl.
  CPC ...... *A63B 22/0221* (2015.10); *A63B 22/0235* (2013.01); *A63B 24/0087* (2013.01); *A63B 69/0064* (2013.01); *A61B 5/1036* (2013.01); *A61B 5/6892* (2013.01); *A63B 2024/0093* (2013.01); *A63B 2220/18* (2013.01); *A63B 2220/52* (2013.01)

(58) Field of Classification Search
  CPC ........ A63B 2220/52; A63B 2024/0093; A63B 2220/18; A61B 5/6892; A61B 5/1036
  USPC ...................................................... 482/51–54
  See application file for complete search history.

(56) References Cited

U.S. PATENT DOCUMENTS

| | | | | |
|---|---|---|---|---|
| 4,423,864 | A * | 1/1984 | Wiik | A63B 22/0012 434/253 |
| 4,733,858 | A * | 3/1988 | Lan | A63B 23/1209 482/113 |
| 5,302,162 | A | 4/1994 | Pasero | |
| 5,314,390 | A * | 5/1994 | Westing | A63B 21/00178 482/111 |
| 5,830,162 | A * | 11/1998 | Giovannetti | A61B 5/1038 482/69 |
| 6,880,487 | B2 * | 4/2005 | Reinkensmeyer | A01K 15/027 119/421 |
| 7,125,388 | B1 * | 10/2006 | Reinkensmeyer | A63B 69/0064 601/23 |
| 7,381,163 | B2 * | 6/2008 | Gordon | A63B 22/02 482/69 |
| 7,621,850 | B2 * | 11/2009 | Piaget | A63B 22/0056 482/54 |
| 8,002,674 | B2 * | 8/2011 | Piaget | A63B 22/0056 482/52 |
| 8,246,354 | B2 | 8/2012 | Chu | |
| 8,262,590 | B2 | 9/2012 | Padula | |
| 8,550,962 | B2 * | 10/2013 | Piaget | A63B 22/0056 482/52 |
| 2006/0052728 | A1 | 3/2006 | Kerrigan | |

OTHER PUBLICATIONS

M. J. Stephens et al, "Loading during the stance phase of walking in humans increases the extensor emg amplitude but does not change the duration of the step cycle," Experimental Brain Research, vol. 124, No. 3, pp. 363-370, 1999.
J. F. Yang et al, "Transient disturbances to one limb produce coordinated, bilateral responses during infant stepping," Journal of neurophysiology, vol. 79, No. 5, pp. 2329-2337, 1998.
V. Dietz et al, "Regulation of bipedal stance: dependency on "load" receptors," Experimental brain research, vol. 89, No. 1, pp. 229-231, 1992.
V. Dietz et al, "Locomotor activity in spinal man: significance of afferent input from joint and load receptors," Brain, vol. 125, No. 12, pp. 2626-2634, 2002.
V. Dietz et al, "Significance of load receptor input during locomotion: a review," Gait & posture, vol. 11, No. 2, pp. 102-110, 2000.
M. Faist et al, "In humans ib facilitation depends on locomotion while suppression of ib inhibition requires loading," Brain research, vol. 1076, No. 1, pp. 87-92, 2006.
Y. P. Ivanenko et al, "Control of foot trajectory in human locomotion: role of ground contact forces in simulated reduced gravity," J. Neurophysiol., vol. 87, pp. 3070-3089, 2002.
M. J. Grey et al, "Positive force feedback in human walking," The Journal of physiology, vol. 581, No. 1, pp. 99-105, 2007.
D. S. Marigold and A. E. Patla, "Adapting locomotion to different surface compliances: neuromuscular responses and changes in movement dynamics," Journal of neurophysiology, vol. 94, No. 3, pp. 1733-1750, 2005.
M. J. MacLellan and A. E. Patla, "Adaptations of walking pattern on a compliant surface to regulate dynamic stability," Experimental brain research, vol. 173, No. 3, pp. 521-530, 2006.
M. D. Chang et al, "Measures of dynamic stability: detecting differences between walking overground and on a compliant surface," Human movement science, vol. 29, No. 6, pp. 977-986, 2010.
T. A. McMahon and P. R. Greene, "The influence of track compliance on running," Journal of biomechanics, vol. 12, No. 12, pp. 893-904, 1979.
A. E. Kerdok, A. A. Biewener, T. A. McMahon, P. G. Weyand, and H. M. Herr, "Energetics and mechanics of human running on surfaces of different stiffnesses," Journal of Applied Physiology, vol. 92, No. 2, pp. 469-478, 2002.
A. Jafari et al, "AwAS-II: A new Actuator with Adjustable Stiffness based on the novel principle of adaptable pivot point and variable lever ratio," in Robotics and Automation (ICRA), 2011 IEEE International Conference on, pp. 4638-4643, 2011.
R. C. Browning, "Effects of obesity and sex on the energetic cost and preferred speed of walking," Journal of Applied Physiology, vol. 100, No. 2, pp. 390-398, 2006.
R. V. Levine and A. Norenzayan, "The pace of life in 31 countries," Journal of cross-cultural psychology, vol. 30, No. 2, pp. 178-205, 1999.
J. Perry, J. R. Davids et al., "Gait analysis: normal and pathological function," Journal of Pediatric Orthopaedics, vol. 12, No. 6, p. 815, 1992.
R. M. Pawar and M. N. Pawar, "Foot length a functional parameter for assessment of height," The Foot, vol. 22, No. 1, pp. 31-34, 2012. Confidential. Limited circulation. For review only. Preprint submitted to 2014 IEEE International Conference on Robotics and Automation. Received Sep. 15, 2013.
C. T. Farley et al, "Mechanism of leg stiffness adjustment for hopping on surfaces of different stiffnesses," Journal of Applied Physiology, vol. 85, No. 3, pp. 1044-1055, 1998.
D. P. Ferris and C. T. Farley, "Interaction of leg stiffness and surface stiffness during human hopping," Journal of applied physiology, vol. 82, No. 1, pp. 15-22, 1997.
D. P. Ferris, K. Liang, and C. T. Farley, "Runners adjust leg stiffness for their first step on a new running surface," Journal of biomechanics, vol. 32, No. 8, pp. 787-794, 1999.
Barkan et al., "Variable stiffness treadmill (VST): a novel tool for the investigation of gait" 2014 IEEE Internation Conference on Robotics & Automation (ICRA), Hong Kong, China, pp. 2838-2843, 2014.
R. Klint et al, "Sudden drop in ground support produces force-related unload response in human overground walking," Journal of neurophysiology, vol. 101, No. 4, pp. 1705-1712, 2009.
K. Nakazawa et al, "On the reflex coactivation of ankle flexor and extensor muscles induced by a sudden drop of support surface during walking in humans," Journal of Applied Physiology, vol. 96, No. 2, pp. 604-611, 2004.
M. H. Van Der Linden et al, "Muscle reflexes and synergies triggered by an unexpected support surface height during walking," Journal of neurophysiology, vol. 97, No. 5, pp. 3639-3650, 2007.
V. Dietz and G. Horstmann, "Interlimb Coordination of Leg-Muscle Activation During Perturbation of Stance in Humans," Journal of neurophysiology, vol. 62, No. 3, pp. 680-693, 1989.
W. Berger et al, "Corrective reactions to stumbling in man: neuronal coordination of bilateral leg muscle activity during gait," Journal of physiology, vol. 357, pp. 109-125, 1984.
W. Berger et al, "Interlimb coordination of posture in man," Journal of physiology, vol. 390, p. 135, 1987.
T. Lam et al, "Stumbling Corrective Responses During Treadmill Elicited Stepping in Human Infants," The Journal of physiology, vol. 553, No. 1, pp. 319-331, 2003.

(56) References Cited

OTHER PUBLICATIONS

K. Boyer, "Changes in muscle activity in response to different impact forces affect soft tissue compartment mechanical properties". Journal of Biomechanical engineering, 2007.
T. Klarner, "Contribution of load and length related manipulations to muscle responses during force perturbations," MS Thesis, University of British Columbia, 2010.
T. Sinkjaer et al, "Major role for sensory feedback in soleus EMG activity in the stance phase of walking in man," The Journal of physiology, vol. 523, No. 3, pp. 817-827, 2000.
P. K. Artemiadis and H. I. Krebs, "On the interlimb coordination and synchronization during gait," in Engineering in Medicine and Biology Society, EMBC, 2011 Annual International Conference of the IEEE. IEEE, 2011, pp. 1571-1574, 2011.
P. K. Artemiadis and H. I. Krebs, "Interlimb coordination evoked by unilateral mechanical perturbation during body-weight supported gait," in Rehabilitation Robotics (ICORR), 2011 IEEE International Conference on. IEEE, 2011, pp. 1-5.
S. Grillner, "The motor infrastructure: from ion channels to neuronal networks," Nature Reviews Neuroscience, vol. 4, No. 7, pp. 573-586, 2003.
Ferris, D.P., et al, "Running in the real world: adjusting leg stiffness for different surfaces," Proc. R. Soc. B, vol. 265, No. 1400, pp. 989-994, 1998.
A. J. Threlkeld et al, "Temporospatial and kinematic gait alterations during treadmill walking with body weight suspension" Gait & Posture, vol. 17, No. 3, pp. 235-245, 2003.
International Search Report and Written Opinion for PCT/US2014/062534, mailed Feb. 2, 2015.

* cited by examiner

VARIABLE STIFFNESS TREADMILL SYSTEM

CROSS REFERENCE TO RELATED APPLICATIONS

This application claims benefit to U.S. provisional patent application Ser. No. 61/896,509 filed on Oct. 28, 2013, which is incorporated by reference in its entirety.

FIELD

The present document relates generally to a treadmill system, and in particular to a variable stiffness treadmill system for controlling the surface stiffness in a precise, repeatable, and extensive manner.

BACKGROUND

Gait requires kinematic and dynamic coordination of the limbs and muscles, multi-sensory fusion and robust control mechanisms. The force stimulus generated by the interaction of the foot with the walking surface is a vital part of the human gait. In human gait motion, there are many forms of stimulus; however, each type of stimulus holds essential information, without which, proper gait motion would be an impossible task. While the effect of load feedback (an important stimulus) on gait has been an active field of study, there is a need for the development of a versatile system that can advance research in this area by providing new functionality.

In previous studies, researchers have utilized compliant surfaces to investigate the effect of load feedback on gait. The simplest setups include surfaces created out of foam of varying stiffness or collegiate gym mats. However, inherent in these setups is the inability to utilize a large range of stiffness while maintaining high resolution (without employing an extreme number of materials). Other devices may have improved the easiness and resolution of compliant walking surfaces, but these designs do not allow for the compliance of the surface to be changed in situ. Moreover, there is no ability to exert a prescribed force perturbation to the foot in real time while an individual is actively walking on the surface.

There are many different methods being employed in contemporary therapeutics, but universal to all rehabilitation processes are several key characteristics. When considering a rehabilitative scenario, it is essential for the system to have the ability to recreate typical stimuli. This technique helps the body recognize and adapt to what would be considered a normal environment. An effective rehabilitation device should take into account all forms of external stimuli that might have an effect on the patient. Another aspect to consider is the precision of the instrument. It is important to be able to quantify the actions of a system in order to effectively characterize the results, and thereby learn about the processes involved. Finally, the system should be able to explore new horizons. Since contemporary techniques are so far away from achieving satisfactory results, it is evident that new methods and systems need to be developed.

BRIEF DESCRIPTION OF THE DRAWINGS

FIG. 8 shows averaged data of hip flexion—extension (FIG. 8A), knee flexion—extension (FIG. 8B), and ankle dorsi—plantar flexion (FIG. 8C) in three cases of treadmill stiffness.

Corresponding reference characters indicate corresponding elements among the view of the drawings. The headings used in the figures do not limit the scope of the claims.

DESCRIPTION

As described herein, a variable stiffness treadmill system having a split-belt treadmill, wherein the surface stiffness of the split-belt treadmill may be controlled in a precise, repeatable, and extensive manner. In particular, the split-belt treadmill controls the variable stiffness to make it suitable for a variety of gait-focused applications, such as research (human gait cycle characteristics, inter-leg coordination, gait reflexes, neurological responses), rehabilitation (the gait-impaired: strokes, neurological disorders, paralysis), and orsimulation (exercise systems, environment simulation).

Referring to the drawings, embodiments of a variable stiffness treadmill (VST) system are illustrated and generally indicated as 100 in FIGS. 1-8. In some embodiments, the VST system 100 may be capable of controlling load feedback stimulus by regulating the walking surface stiffness in real time. In addition, the VST system 100 provides a high range of available stiffness, resolution and accuracy, as well as the ability to regulate stiffness within the stance phase of walking. The VST system 100 may also constitute a useful research tool, which may improve our understanding of gait and create new avenues of research on gait analysis and rehabilitation.

In some embodiments, the VST system 100 may include a split-belt treadmill 108 including a first belt 119 and a second belt 121 configured to engage the left foot and the right foot, respectively, of the individual in contact with the split-belt treadmill 108 mounted on a platform 103. In an aspect, the split-belt treadmill 108 may be lifted with a frame of steel tubing. Since the individual platforms of the split-belt treadmill 108 are free to rotate about a common axis, it may be possible to achieve the downward displacement necessary to induce a range of stiffness on the surface. Additionally, the opposability of the split-belt treadmill 108 may allow for the adjustment of one side at a time.

In one arrangement, the configuration of the split-belt treadmill 108 allows each respective belt 119 and 121 to deflect different amounts, thereby allowing different force perturbations to be applied to each leg. In an aspect, the treadmill belts may be supported at about 70 cm above the floor to permit each belt to independently deflect downward to a maximum of about 30° from the horizontal position. The adjustability of the treadmill stiffness may be limited to only one belt, but may be applied to both sides by installing another variable stiffness mechanism 102.

Figure 2A:
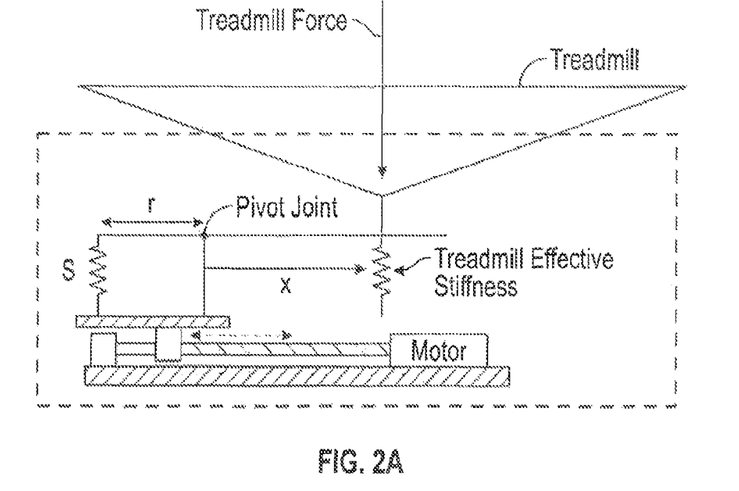
FIG. 2A is a conceptual diagram of a variable stiffness mechanism for the variable stiffness treadmill system.
Figure 2B:
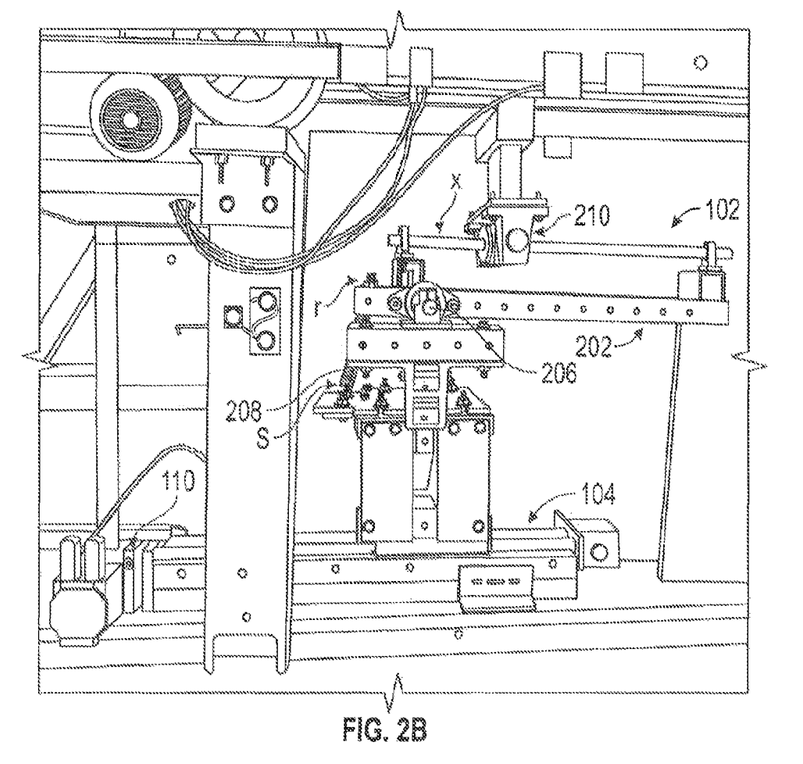
FIG. 2B is a photograph of one setup of the variable stiffness mechanism of FIG. 2A.

Beneath the split-belt treadmill 108 may be a variable stiffness mechanism 102 that produces and controls the stiffness of the surface above it. The variable stiffness mechanism 102 may vary the vertical stiffness of the walking surface (i.e. treadmill), therefore controlling the force interaction between the individual and the walking surface of the split-belt treadmill 108. The capability of the VST system 100 to achieve a large range of controllable stiffness with high resolution comes from the variable stiffness mechanism 102. In its most simplified form, the variable stiffness mechanism 102 may include a spring-loaded lever 202 mounted on a linear track 104, as shown in FIG. 2. The effective stiffness of the split-belt treadmill 108, located at a distance x from the pivot joint 206, is dependent on the coefficient of stiffness S of the springs 208 and the moment arm r through which it exerts a force. By design, S and r remain constant, therefore, the effective stiffness of the treadmill can be controlled by changing the distance x.

In one embodiment, the spring-loaded lever 202 may be made mostly from aluminum rectangular tubing that may be fastened to the carriage of a high-precision linear track 104. Two high-capacity extension springs 208 may exact stiffness about one side of the spring-loaded lever 202 while the opposing side of the spring-loaded lever 202 may be connected via a sliding joint 210 to the split-belt treadmill 108 above it. This component allows for the transmission of forces across the spring-loaded lever 202 from the springs 208 to the split-belt treadmill 108.

As the spring-loaded lever 202 is deflected by the displacement of the split-belt treadmill 108, the springs 208 on the opposing side of the spring-loaded lever 202 may be extended. The degree to which the force is transmitted is directly related to the moment arm between a pivot joint 206 of the spring-loaded lever 202 and the connection points on either side of the spring-loaded lever 202. By varying the length of the moment arm that separates the pivot joint 206 and the sliding joint 210 of the platform 103, the transmitted stiffness can also be varied. This process may be achieved by adjusting the linear track 104 upon which the variable stiffness mechanism 102 is situated. The sliding joint 210 between the split-belt treadmill 108 and the arm of the spring-loaded lever 202 may be a sliding joint 210 that rides along a linear rail, which may be mounted on to the arm of the spring-loaded lever 202. As the linear track 104 is actuated in a particular direction, the internal mechanism may go with it, and the moment arm between the sliding joint 210 and the pivot joint 206 may be altered as a result. In this way, adjusting the displacement of the linear track 104 may control the apparent stiffness felt at the surface of the split-belt treadmill 108.

In order to keep the split-belt treadmill 108 level, a counterweight system 112 may attach to the split-belt treadmill 108 to extend to the opposite side axis of rotation for the split-belt treadmill 108. The counterweight system 112 may be composed of steel rectangular tubing and may have an aluminum component for mounting weight at a specific point along the counterweight system 112.

Referring back to FIG. 1A, the VST system 100 may include a force sensor mat 106 to track the location of the individual's foot along the first and second belts 119 and 121 of the split-belt treadmill 108. In some embodiments, the force sensor mat 106 may include an array of force sensing resistors located beneath the each of the first and second belts 119 and 121. For example, eight force sensing resistors may be included in the force sensor mat 106 such that whichever sensor is underneath the center of pressure of the foot should give the highest force reading. Without being limited to a particular theory, when two sensors give similar high force measurements, it may be assumed that the center of pressure is between the two sensors. In one aspect, the force sensor mat 106 may span about 80 cm, with eight sensors, so there may be a spatial resolution of about 5 cm. For example, assuming the average human foot length is about 23.5 cm, this resolution may be sufficient to ascertain the location of the foot. As shown in the mathematical derivation in Example 3, the foot position may be used as an input to calculate the corresponding linear track position that may create the proper apparent stiffness beneath the individual.

In some embodiments, the VST system 100 may include a treadmill motor 110. In an aspect, the treadmill motor 110 may be a 1-HP variable speed DC motor that may drive the first and second belts 119 and 121 of the split-level treadmill 108. The treadmill motor 110 may obtain speeds of up to about 1.85 m/s at a resolution of about 7 mm/s which includes the average preferred walking speed of about 1.2-1.4 m/s, but may be slowed for individuals in therapy or rehabilitation applications.

Figure 1A:
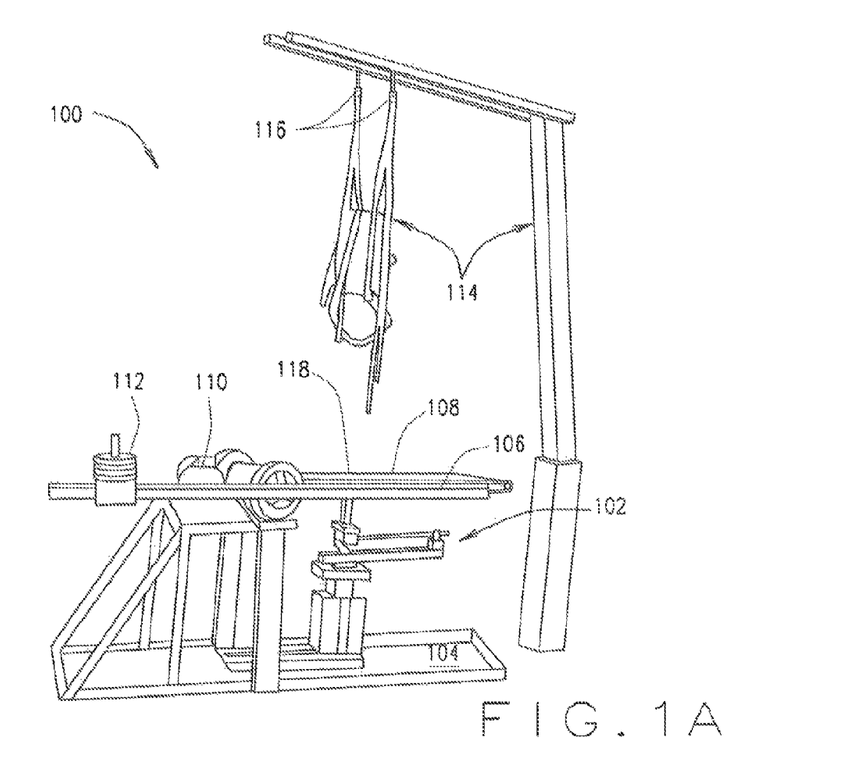
FIG. 1A is a photograph of a variable stiffness treadmill system.

In some embodiments, the VST system 100 may include an inclinometer 118 that provides a means for measuring the angle of elevation of the split-belt treadmill 108 as illustrated in FIG. 1A.

Figure 1B:
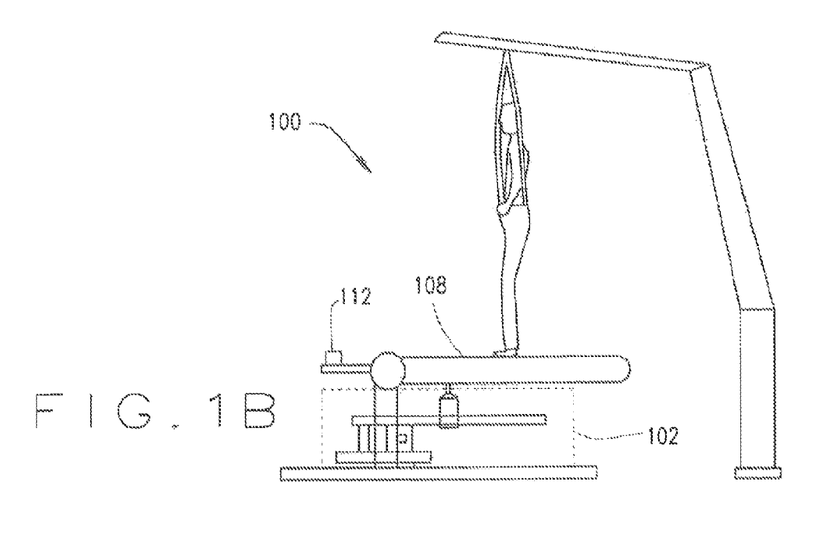
FIG. 1B is conceptual diagram of the variable stiffness treadmill system of FIG. 1A.

Referring to FIGS. 1A and 1B, the VST system 100 may further include a counterweight system 112 to ensure accurate control of treadmill stiffness and eliminate moments from the weight of the split-belt treadmill 108. This may be achieved by fastening a weighted slider 113 at the precise location along a co-linear beam 111 which may induce an equal and opposite moment to that of the split-belt treadmill 108. This co-linear beam 111 may be attached to the side of the split-belt treadmill 108 so that the counterweight system 112 may cancel out the weight of the split-belt treadmill 108 at any inclination.

In some embodiments, the VST system 100 may include a body-weight support 114 that is mounted to a rail 117 connected to a post 115, which is separate from the treadmill platform 103. The body-weight support 114 may be a harness or other type of wearable component configured to be worn by an individual using the split-belt treadmill 108. By adjusting the height of the rail 117 along the post 115, full or partial body-weight support may be selected. This adjustment of the rail 117 can reduce ground reaction forces to allow more accurate control of force perturbations. In addition, the body-weight support 114 may increase safety and extend the VST system's 100 capabilities to stroke patients and other individuals with decreased mobility and stability. In some embodiments, two loadcells 116 may be attached on the body weight support 114 harness to measure the individual weight supported by the variable stiffness mechanism 102 from each side.

The VST system 100 may alter the walking surface stiffness in real time, offering a wide range of available stiffness, practically from infinite stiffness (non-compliant walking surface) to as low as about 61.7 N/m. The resolution of the controlled stiffness may research a maximum of about 0.038 N/m, while the effective stiffness may change from maximum to minimum in about 0.13 s. Unlike previous devices, the VST system 100 is capable of creating any profile of stiffness during an experiment and throughout the gait cycle.

The VST system 100 may have a wide range of controllable stiffness (essentially zero to infinite), but may maintain high resolution. It may have the ability to actively vary and control the compliance of the treadmill surface within the gait cycle. By measuring the displacement of the walking surface (e.g., the first and second belts 119 and 121), the load force exerted on the foot to the split-belt treadmill 108 may be estimated, and a force may be exerted on the foot by adjusting the stiffness in real-time. The above elements allow for a better understanding of gait. The VST system 100 may allow for a large range of selectable stiffness throughout the gait cycle, as well as for full-continuous control of that stiffness during the stance phase. This allows the introduction of a plethora of force perturbations to the leg that may be difficult to implement with current devices.

Apart from a unique research tool, the VST system 100 may be applied for gait rehabilitation. The ability to apply perturbations and regulate force feedback allows for the definition of rehabilitation protocols beyond the state of the art, where the interplay of the leg dynamics with a dynamic environment may play a major role. Moreover, the VST system 100 may be used as a simulation-testing system for biological and artificial walkers, when investigating walking patterns and architectures in environments of variable stiffness is required.

EXAMPLES

Example 1

Design Characteristics

It has been found that the VST system 100 achieves greater versatility and functionality than other devices by combining a variety of components into one unique system. The VST system 100 is shown in FIG. 1. As noted above, the major components of the VST system 100 include a variable stiffness mechanism 102, a linear track 104 (Thomson Linear Inc), a force sensor mat 106, a split-belt treadmill 108, a DC treadmill motor 110 (Anaheim Automation), a counterweight system 112, and a custom-built body weight support (LiteGait) with two load cells 116 measuring the individual's weight supported by the system. Each component is important to the VST system 100 for the overall function and proper investigation of gait, and will be analyzed below.

Example 2

Variable Stiffness Mechanism

In order to get the desired range of stiffness, the variable stiffness mechanism (FIG. 2) was built with two extension springs of stiffness k=5122 N/m, rest length of 12.7 cm and outside diameter of 2.54 cm (LE 135J 06 M, Lee Spring Co.). The two springs 208 were combined in parallel, at a distance of 7.5 cm from the pivot point. The spring stiffness was chosen to meet the specification for the range of effective treadmill stiffness, which is analyzed below.

This entire assembly sits on the carriage of a high-capacity linear track 104 (Thomson Linear, Part Number: 2RE16-150537) which is controlled by a high-precision drive (Kollmorgen, Part Number: AKD-P00606-NAEC-0000) and has a translational resolution of 0.01 mm. This results in a high resolution for the adjustment of effective stiffness that is discussed below.

In addition to achieving the desired range and resolution of stiffness with the variable stiffness mechanism 102, the treadmill stiffness was actively varied throughout the gait cycle. In the most extreme scenario of going from a rigid surface, i.e. treadmill stiffness of $K_t=\infty$, to the minimum achievable stiffness, the linear track will have to move across its entire range (0 to 40 cm). Considering the fact that the linear track 104 can move as fast as 3 m/s, the system could make this extreme change in stiffness in 0.13 s. Assuming that the individual is walking at a normal pace of 1.4 m/s, with a stride length (the distance between consecutive points of initial contact by the same foot) of 1.4 m, the stance phase would last approx. 0.5 s. This means that the variable stiffness mechanism 102 can make this extreme change in stiffness three times during the stance phase. Therefore, it can easily change stiffness many times throughout the gait cycle when the desired change in stiffness is smaller than the two extremes. The ability to change stiffness at a high rate throughout the stance phase of the gait cycle adds to the unique capabilities of the VST system 100.

Example 3

Governing Equations

Figure 3A:
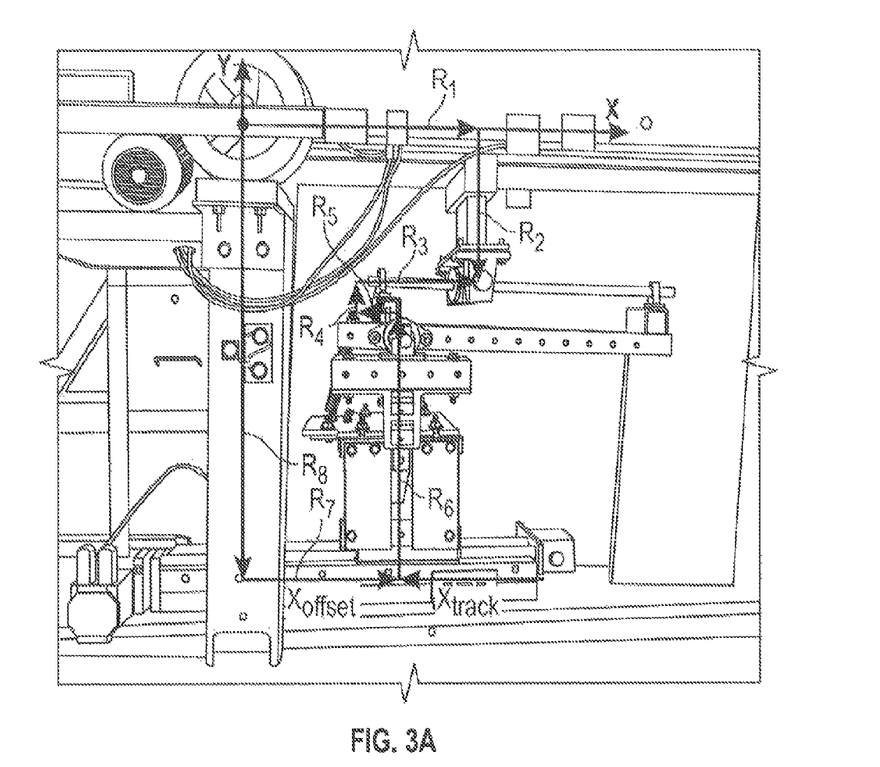
FIG. 3A is a photograph of the variable stiffness mechanism with the kinematic analysis of FIG. 3B superimposed on the photograph of FIG. 3A.
Figure 3B:
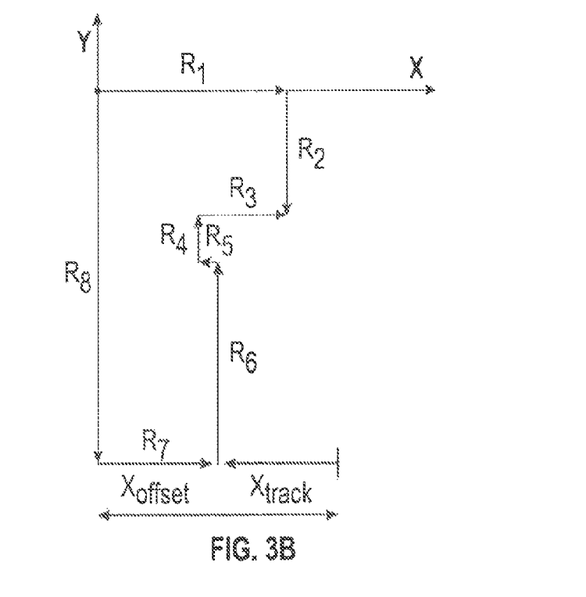

1) Kinematics: A kinematic analysis of the VST system 100 was performed in order to create a mathematical model relating the measured inputs: angular deflection of the treadmill ($\theta_1$), linear track position ($x_{track}$), and foot position ($x_f$), to the effective treadmill stiffness at the location of the foot. To accomplish this, the vector loop shown in FIG. 3 was created based off of the rigid body structure of the VST system. The vector loop equations are given by:

$$R_1+R_2=R_8+R_7+R_6+R_5+R_4+R_3 \quad \text{Eqn. (I)}$$

where $R_i$, i=1, 2, . . . , 8 are the vectors shown in FIG. 3. Resolving this vector equation into its x and y components using the reference system shown in FIG. 3:

$$\sum_{i=1,2} \|R_i\|\cos(\theta_i) = \sum_{m=3,4,5,6,7,8} \|R_m\|\cos(\theta_m) \quad \text{Eqn. (II)}$$

$$\sum_{i=1,2} \|R_i\|\sin(\theta_i) = \sum_{m=3,4,5,6,7,8} \|R_m\|\sin(\theta_m)$$

where $\theta_i$, i=1, 2, . . . , 8 are the angles of the vectors $R_i$, i=1, 2, . . . , 8 from the positive x-axis, measured counterclockwise. Some of the vectors are not rotating due to structural constraints listed in Table I.

TABLE I

| KINEMATIC CONTRAINTS | | | |
|---|---|---|---|
| Vector magnitudes (m) | | Vector angles (rad) | |
| $\|R_1\|$ | 0.33 | $\theta_6$ | $\frac{\pi}{2}$ |
| $\|R_2\|$ | 0.18 | $\theta_7$ | 0 |
| $\|R_4\|$ | 0.085 | $\theta_8$ | $\frac{-\pi}{2}$ |
| $\|R_5\|$ | 0.02 | $\theta_{3a}$ | 0 |

TABLE I-continued

KINEMATIC CONTRAINTS

| Vector magnitudes (m) | | Vector angles (rad) | |
|---|---|---|---|
| $\|R_6\|$ | 0.44 | $\theta_{4a}$ | $\frac{\pi}{2}$ |
| $\|R_8\|$ | 0.705 | $\theta_2$ | $\theta_1 - \frac{\pi}{2}$ |
| $\|R_{2a}\|$ | 0.075 | $\theta_5$ | $\theta_3 - \pi$ |
| $\|R_{3a}\|$ | 0.11 | $\theta_4$ | $\theta_3 + \frac{\pi}{2}$ |
| $x_{offset}$ | 0.325 | | |
| $\|R_{4a}\|$ | 0.12 | $\theta_{2a}$ | $\theta_3$ |
| $\|R_7\|$ | $x_{offset} - x_{track}$ | | |

Figure 4A:
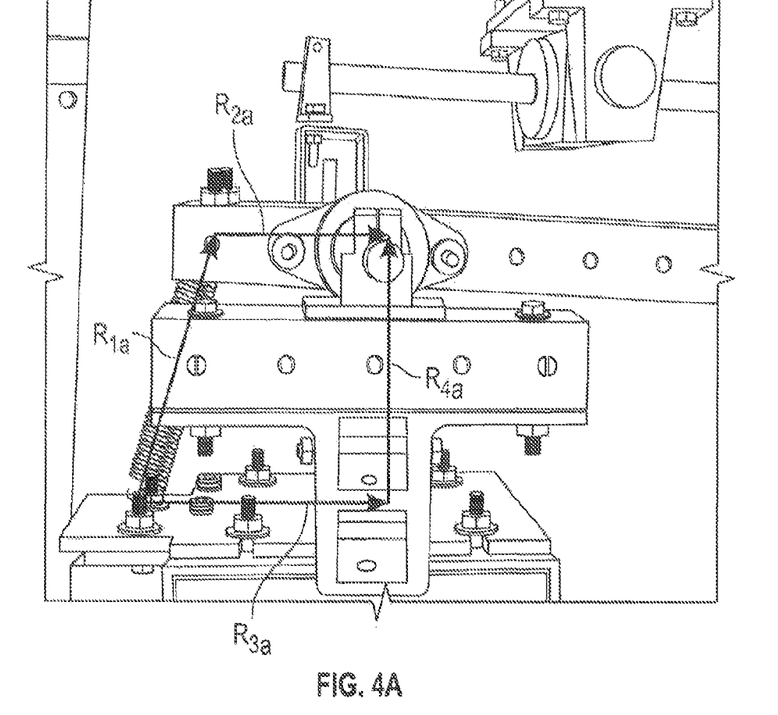
FIG. 4A is a photograph of the spring mechanism with the kinematic analysis of FIG. 4B superimposed on the photograph of FIG. 4A.
Figure 4B:
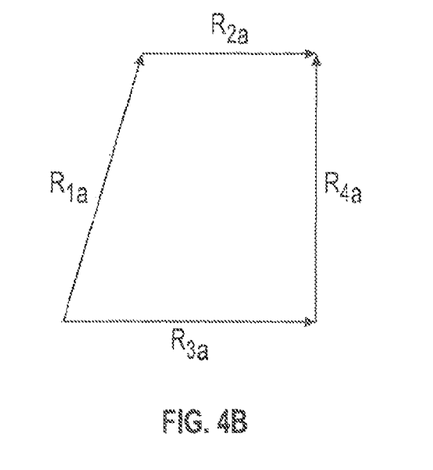

Because of this, the kinematic equations in Eqn. (II) are simplified to:

$$\|R_1\|c_1 + \|R_2\|s_1 = x_{offset} - x_{track} - \|R_5\|c_3 - \|R_4\|s_3 + \|R_3\|c_3 \|R_1\|s_1 - \|R_2\|c_1 = -\|R_8\| + R_6\| - \|R_5\|s_3 + \|R_4\|c_3 + \|R_3\|s_3 \quad \text{Eqn. (III)}$$

where $c_i$, $s_i$ correspond to cos $(\theta_i)$ and sin $(\theta_i)$ respectively, and $x_{offset}$ is the known horizontal distance from the rotation point of the treadmill to the zero position of the linear track. These two equations were then solved for the two unknown variables $\|R_3\|$ and $\theta_3$ in terms of the inputs $\theta_1$ and $x_{track}$. It must be noted that an inclinometer was used in order to measure the treadmill angular deflection $\theta_1$, while the position of the linear track $x_{track}$ is controlled in real-time in order to achieve the desired stiffness. The same method was used in order to describe the kinematics of the spring mechanism, as shown in FIG. 4. The final equations that were solved for the two unknowns $\|R_{1a}\|$ and $\theta_{1a}$ are given by:

$$\|R_{1a}\|\cos(\theta_{1a}) + \|R_{2a}\|\cos(\theta_3) = \|R_{3a}\| \|R_{1a}\|\sin(\theta_{1a}) + \|R_{2a}\|\sin(\theta_3) = \|R_{4a}\| \quad \text{Eqn. (IV)}$$

wherein all vectors are shown in FIG. 4, along with their correspondence to the real system features.

Figure 5A:
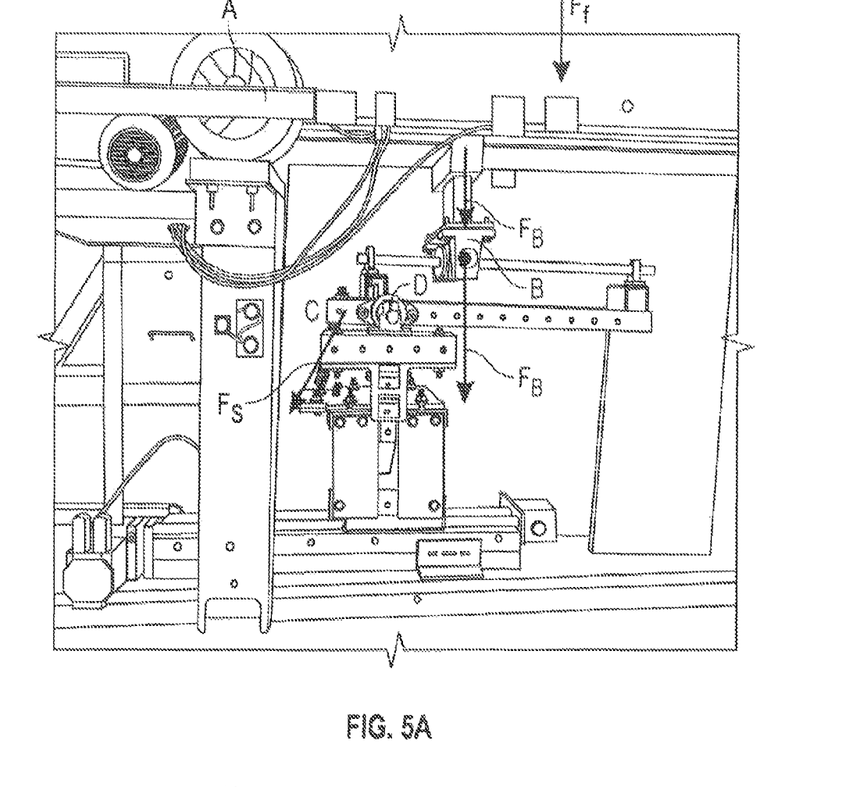
FIG. 5A is a photograph of the variable stiffness mechanism with the kinematic analysis of FIG. 5B superimposed on the photograph of FIG. 5A, where $F_f$ is the force exerted by the individual's foot, at a distance $x_f$ from the rotation point of the treadmill, $F_s$ is the spring force, and $F_B$ the force at the sliding joint B.
Figure 5B:
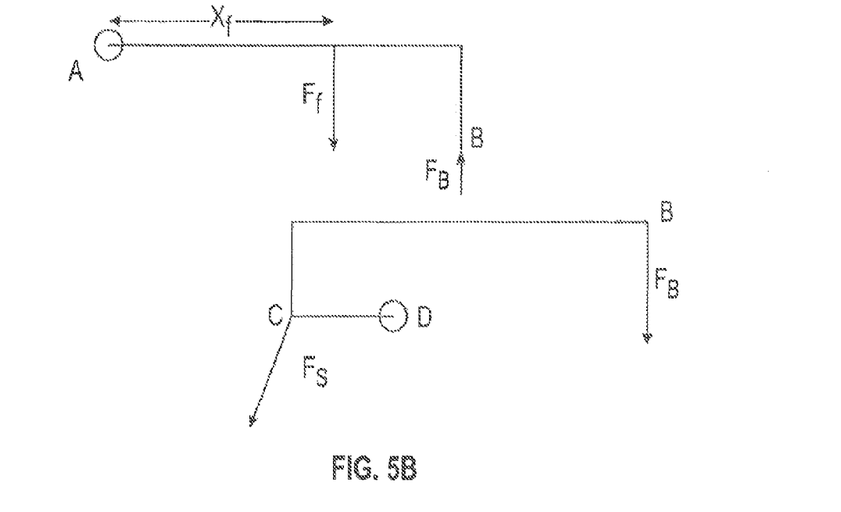

2) Kinetics: The final step in the mathematical model of the VST system 100 was to use the solutions of unknown variables from the kinematic analysis and apply them to the equilibrium equations for the free body diagrams of the VST system 100, as shown in FIG. 5. $F_s$ is the force exerted by the spring. Since the connection point at B is a sliding joint, the force that it transmits at mechanical equilibrium can only be perpendicular to the sliding axis along $R_3$. This allowed the calculation of the transmitted force $F_B$ with the following moment equation about location D.

$$\Sigma M_D = F_a \|R_{2a}\|\sin(\theta_3 - \theta_{1a}) - F_B(\|R_3\| - \|R_5\|) = 0 \quad \text{Eqn. (V)}$$

where $F_s = 2k(\|R_{1a}\| - l_0)$ is the force from the springs and $l_0$ is the rest length of the two springs used, each one having a stiffness k. The calculated value for $F_B$ was used to solve for the force of the foot $F_f$ in the equilibrium equation about point A:

$$\Sigma M_A = F_B \|R_1\|\cos(\theta_3 - \theta_1) - F_B \|R_2\|\sin(\theta_3 - \theta_1) - F_f x_f \cos(\theta_1) = 0 \quad \text{Eqn. (VI)}$$

Then, the effective stiffness of the treadmill $k_t$ is finally computed by:

$$k_t = \frac{F_f}{x_f \tan(\theta_1)} \quad \text{Eqn. (VII)}$$

The mathematical derivation above shows that the effective treadmill stiffness at the location of the individual's foot can be calculated by measuring the angle of the treadmill deflection $\theta_1$, the foot position $x_f$ and the track position $x_{track}$. The latter is something that may be controlled, therefore, given the position of the individual's foot and the angular deflection of the treadmill, the control variable of the system is the position of the track $x_{track}$.

The range of the control of the track position will define the range of the treadmill effective stiffness that can be achieved. For $x_{track} = 0$, the treadmill stiffness is practically infinite, since the treadmill cannot be deflected. For the maximum displacement of the track of 40 cm, the computed treadmill stiffness, assuming that the foot of the individual is approximately in the middle of the treadmill (i.e. during mid-stance), is 585.5 N/m. At the end of the treadmill (i.e. at toe-off phase), the minimum achievable stiffness is 61.7 N/m.

Figure 6:
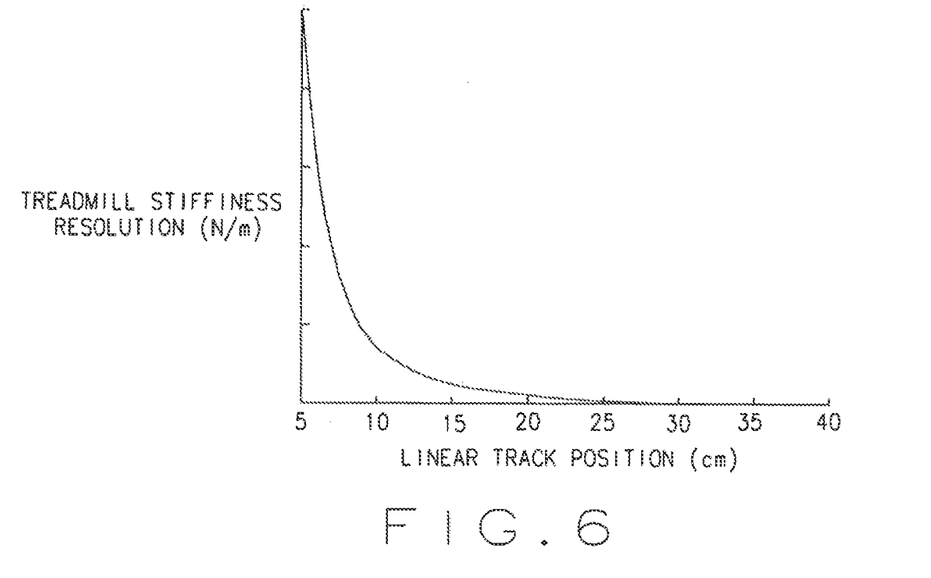
FIG. 6 shows treadmill stiffness resolution as a function of the linear track position.

The resolution of achievable displacement of the linear track 104 is 0.01 mm. Since the relationship between the linear track position and the treadmill effective stiffness in non-linear, the resolution of achievable treadmill stiffness is dependent on the linear track position. By solving the aforementioned equations and using the given linear track resolution, the resolution was computed for stiffness for any given linear track position. This solution curve is depicted in FIG. 6, where it is shown that the resolution of stiffness can range from 9.06 N/m when the linear track is at 5 cm, to 0.038 N/m when the linear track is at its maximum displacement of 40 cm. Lower resolution is achieved for position between 0 and 5 cm of the linear track 104, as stiffness grows to infinity.

Example 4

Experimental Validation

Figure 7:
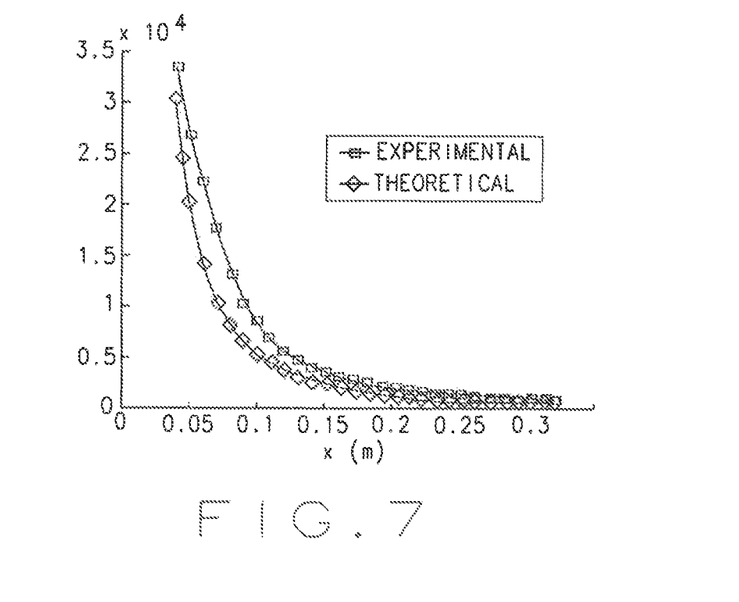
FIG. 7 shows experimental versus theoretical values of treadmill effective stiffness.

The results obtained from the mathematical model were compared to experimental data for validation. The apparent stiffness of the split-belt treadmill 108 for 1 cm interval displacements of the linear track 104 was found by placing a known mass (4.5 kg) at a known distance (0.33 m) along the split-belt treadmill 108 and measuring the angular displacement of the split-belt treadmill 108. This process resulted in a plot of stiffness vs. the track position. The resulting curve was compared to the theoretical model where the foot position $x_f$ was defined as 0.33 m to match the experimental setup. The results are shown in FIG. 7. It can be observed that both models achieve the same type of inverse square power profile and converge at low stiffnesses. The slightly higher stiffness values from the experimental data in parts of the domain may reflect the fact that friction is not accounted for in the theoretical model. Friction would cause a decrease in deflection for a given force resulting in higher stiffness values than a frictionless model. However, the theoretical model matched the experimental one very well, proving the validity of the system. This plot also gives an indication of the range of achievable stiffness as a function of the linear track position.

Example 5

Testing in Healthy Individuals

In order to test the VST system 100 with healthy individuals and to validate its performance, experimental studies were conducted as "proof of concept" for the VST system 100. For preliminary experiments, two healthy males walked on the treadmill moving at a comfortably slow speed of 0.3 m/s with three different treadmill stiffnesses: 100, 60, and 20 kN/m. This range resembles that of other variable stiffness devices. The stiffness was kept constant throughout the gait cycle. The provided body weight supported was controlled at approx. 40%. The kinematic data was obtained using a motion capture system (3D Investigator, Northern Digital) that was used to track five markers located at the torso, hip, knee, ankle, and toe in order to calculate the joint angles throughout the gait cycle.

Figure 8A:
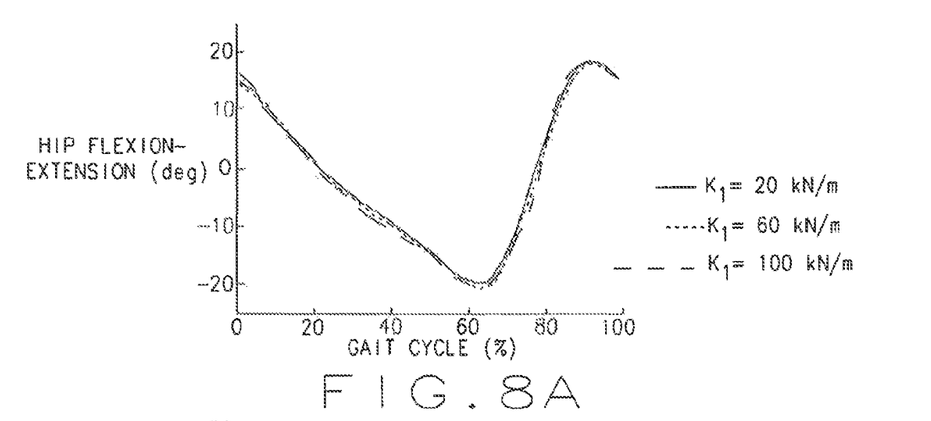
Figure 8B:
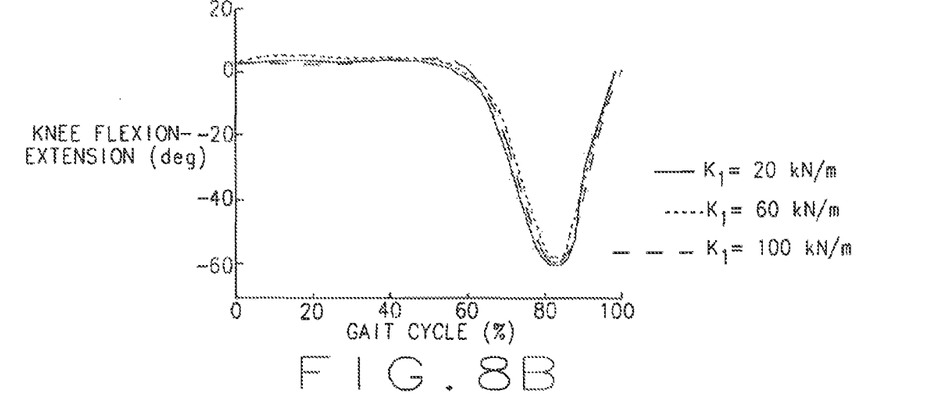
Figure 8C:
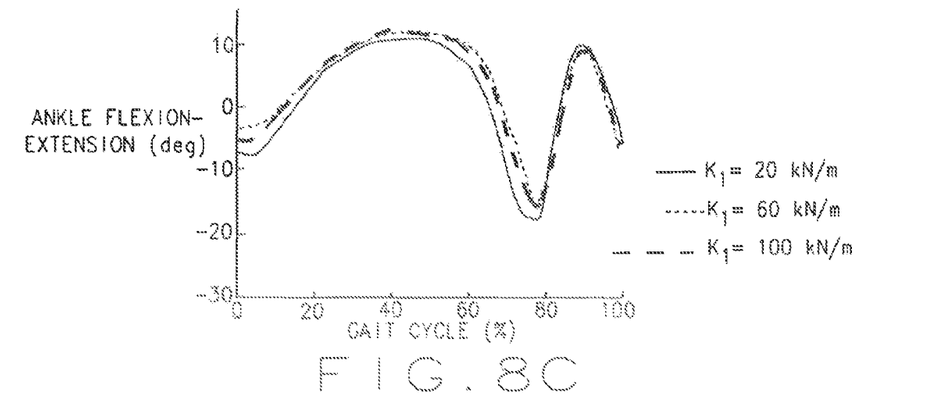

The averaged kinematic data across both individuals is shown in FIG. 8. The hip flexion-extension, knee flexion-extension and ankle dorsi/plantar flexion are shown (mean and standard deviation across all gait cycles). The data is plotted as a function of the gait cycle percentage, where 0% corresponds to heel-strike, 60% corresponds to toe-off etc. As can be seen, the joint angle profiles resemble that of normal gait, therefore the VST system 100 did not alter the normal gait kinematics. The knee and hip kinematics appear to be unaffected by the effective treadmill stiffness changes, while the ankle joint appears to have some systematic increased plantar flexion before toe-off, as the effective treadmill stiffness is lowered. This is expected since the loading of the foot between heel-off and toe-off will press the treadmill downwards at lower stiffness, and therefore the ankle will need to plantar-flex more.

What is claimed is:

1. A variable stiffness treadmill system comprising:
   an elevated split-belt treadmill comprising of a first belt and a second belt;
   a motor operatively connected to the split-belt treadmill for driving the first and second belts of the split-belt treadmill;
   a variable stiffness mechanism operatively connected to the split-belt treadmill for varying the vertical stiffness of the first belt and the second belt, the variable stiffness mechanism comprising:
      a linear track; and
      a spring-loaded lever operatively connected to the linear track;
   a counterweight system operatively connected to the split-belt treadmill to counter balance the weight of an individual on the split-belt treadmill; and
   a body-weight support mounted to a post, the body weight support capable of supporting the weight of the individual relative to the post, wherein the spring-loaded lever is adjustable to vary the stiffness of the elevated split-belt treadmill.

2. The variable stiffness treadmill system of claim 1, further comprising:
   an inclinometer is operatively connected to the split-belt treadmill for the measurement of the inclination of the split-belt treadmill relative to an underlying surface.

3. The variable stiffness treadmill system of claim 1, wherein the post is engaged to a rail for mounting the body-weight support.

4. The variable stiffness treadmill system of claim 1, wherein the body weight support comprises a harness.

5. The variable stiffness treadmill system of claim 4, wherein the harness further comprises at least one loadcell for measuring the weight of the individual engaged to the body-weight support.

6. The variable stiffness treadmill system of claim 1, wherein the first belt and the second belt of the split-belt treadmill are each supported at about 70 cm above the floor and each independently deflect downward to a maximum of about 30° from a horizontal position.

7. The variable stiffness treadmill system of claim 1, wherein the stiffness of the first belt and the second belt may be adjusted independently.

8. The variable stiffness treadmill system of claim 1, further comprising:
   a sliding joint operatively connected between the split-belt treadmill and the spring-loaded lever, wherein the sliding joint is engaged to the linear rail on the spring-loaded lever.

9. The variable stiffness treadmill system of claim 1, further comprising:
   a force sensor mat operatively connected to the split-belt treadmill for sensing the location of an individual in contact with the first belt and the second belt.

10. The variable stiffness treadmill system of claim 1, wherein the stiffness of the first belt and the second belt ranges from about infinite stiffness to about 62 N/m.

11. The variable stiffness treadmill system of claim 1, wherein the maximum resolution of the stiffness is about 0.038 N/m.

12. A method of using a variable stiffness treadmill system comprising:
   placing an individual on the variable stiffness treadmill system comprising:
      an elevated split-belt treadmill comprising of a first belt and a second belt;
      a motor operatively connected to the split-belt treadmill for driving the first and second belts of the split-belt treadmill;
      a variable stiffness mechanism operatively connected to the split-belt treadmill for varying the vertical stiffness of the first belt and the second belt, the variable stiffness mechanism comprising:
         a linear track; and
         a spring-loaded lever operatively connected to the linear track;
      a counterweight system operatively connected to the split-belt treadmill to counter balance the weight of an individual on the split-belt treadmill; and
      a body-weight support mounted to a post, the body weight support capable of supporting the weight of the individual relative to the post, wherein the spring-loaded lever is adjustable to vary the stiffness of the elevated split-belt treadmill;
   attaching a body-weight support to the individual;
   mounting the body-weight support to a frame positioned above the split-belt treadmill;
   measuring the location of the individual with a force sensor mat positioned adjacent the first belt and the second belt; and
   adjusting the vertical stiffness of the first belt and/or second belt below the location of the individual with the variable stiffness mechanism.

13. The method of claim 12, wherein the stiffness of the split-belt treadmill is regulated in real time.

14. The method of claim 13, wherein the stiffness of the split-belt treadmill is adjusted by a spring-loaded lever in the variable stiffness mechanism.

15. The method of claim 13, further comprising:
   measuring the weight of an individual supported by the support with at least one loadcell on the body weight support.

16. The method of claim 12, further comprising:
   counter balancing the split-belt treadmill with the counterweight system.

17. The method of claim 12, wherein the height of the support relative to the split-belt treadmill is adjusted to vary the amount of weight of the individual being supported by the body-weight support.

18. The method of claim 12, further comprising:
    measuring the inclination of the split-belt treadmill with an inclinometer operatively connected to the split-belt treadmill.

19. The method of claim 12, wherein the stiffness of the first belt and the second belt is adjusted independently.

20. The method of claim 12, wherein the variable stiffness mechanism provides for selecting degree of stiffness imparted to the split-beam treadmill throughout a gait cycle of the individual and for continuous controlling of the stiffness during a stance phase of the individual.

\* \* \* \* \*